United States Patent
Addy et al.

(10) Patent No.: US 11,365,316 B2
(45) Date of Patent: *Jun. 21, 2022

(54) WAX ESTER COMPOSITIONS AND METHODS OF MANUFACTURE

(71) Applicant: International Flora Technologies, Ltd., Chandler, AZ (US)

(72) Inventors: Jeff Addy, Chandler, AZ (US); James Steven Brown, Chandler, AZ (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/525,422

(22) Filed: Jul. 29, 2019

(65) Prior Publication Data

US 2019/0345336 A1  Nov. 14, 2019

Related U.S. Application Data

(63) Continuation of application No. 15/594,908, filed on May 15, 2017, now Pat. No. 10,364,354.

(51) Int. Cl.
| | | |
|---|---|---|
| *C08L 91/06* | (2006.01) | |
| *C11C 3/00* | (2006.01) | |
| *C08K 5/01* | (2006.01) | |
| *C10M 159/12* | (2006.01) | |
| *C12P 7/6436* | (2022.01) | |

(52) U.S. Cl.
CPC ............ *C08L 91/06* (2013.01); *C08K 5/01* (2013.01); *C10M 159/12* (2013.01); *C11C 3/003* (2013.01); *C12P 7/6436* (2013.01); *C10M 2207/281* (2013.01)

(58) Field of Classification Search
CPC ............ C10M 159/12; C10M 2207/40; C10M 2207/281; C10N 2010/02; C11C 3/003; C08K 5/01
See application file for complete search history.

(56) References Cited

U.S. PATENT DOCUMENTS

| | | | | |
|---|---|---|---|---|
| 4,510,093 A | * | 4/1985 | Hulsmann | ................. C11C 3/00 554/223 |
| RE38,141 E | * | 6/2003 | Brown | ..................... A61K 8/02 424/401 |

(Continued)

FOREIGN PATENT DOCUMENTS

| | | |
|---|---|---|
| WO | 2015128829 A1 | 9/2015 |
| WO | 2016100957 A1 | 6/2016 |

OTHER PUBLICATIONS

International Search Report & Written Opinion, PCT Patent Application No. PCT/US2018/032545, dated Aug. 8, 2018, 9 pages.

(Continued)

*Primary Examiner* — James C Goloboy

(57) ABSTRACT

Implementations of wax ester compositions may include: a product of transesterifying oleyl oleate, stearyl stearate, and behenyl behenate using one of a chemical or an enzyme catalyst. The ratio of the oleyl oleate to stearyl stearate to behenyl behenate in the mixture prior to transesterification is one of 65%/23%/12%, 56%/29%/15%, or 36%/34%/30%, respectively, measured by weight. The product may demonstrate a substantially equivalent physical property to a physical property of a transesterified wax ester composition including a jojoba ester.

10 Claims, 5 Drawing Sheets

(56) References Cited

U.S. PATENT DOCUMENTS

| | | | |
|---|---|---|---|
| 10,364,354 B2 * | 7/2019 | Addy | C08L 91/06 |
| 2004/0221503 A1 | 11/2004 | Murphy et al. | |
| 2007/0154432 A1 | 7/2007 | Davis | |
| 2010/0215610 A1 | 8/2010 | Anantaneni et al. | |
| 2014/0105947 A1 | 4/2014 | Schlossman et al. | |
| 2016/0177350 A1 | 6/2016 | Addy et al. | |

OTHER PUBLICATIONS

Anonymous: "Floraesters 20, product specifications", Jan. 1, 2019 (Jan. 1, 2019), pp. 1-1, XP055765563, Retrieved from the Internet: URL:https://www.floratech.com/PDFs/SpecSheets/SP_E1_A020.pdf [retrieved on Jan. 15, 2021].

Anonymous: "Floraesters 30, product specifications", Jan. 1, 2019 (Jan. 1, 2019), pp. 1-1, XP055765564, Retrieved from the Internet: URL:https://www.floratech.com/PDFs/SpecSheets/SP_E1_A030.pdf [retrieved on Jan. 15, 2021].

Anonymous: "Floraesters 60, product specifications", Jan. 1, 2019 (Jan. 1, 2019), pp. 1-1, XP055765565, Retrieved from the Internet: URL:https://www.floratech.com/PDFs/SpecSheets/SP_E1_A060.pdf [retrieved on Jan. 15, 2021].

Anonymous: "Jojoba oil", Jan. 13, 2021 (Jan. 13, 2021), pp. 1-5, XP055765578, Retrieved from the Internet: URL:https://en.wikipedia.org/wiki/Jojoba_oil [retrieved on Jan. 15, 2021].

Anonymous: "Jojoba ester", Wikipedia, Nov. 25, 2020 (Nov. 25, 2020), pp. 1-2, XP055765582, DOI: 10.1126/sciadv.aay3240 Retrieved from the Internet: URL:https://en.wikipedia.org/wiki/Jojoba_ester [retrieved on Jan. 15, 2021].

* cited by examiner

WAX ESTER COMPOSITIONS AND METHODS OF MANUFACTURE

CROSS REFERENCE TO RELATED APPLICATIONS

This application is a continuation application of the earlier U.S. Utility patent application to Jeff Addy entitled "Wax Ester Compositions and Methods of Manufacture," application Ser. No. 15/594,908, filed May 15, 2017, the disclosure of which is hereby incorporated entirely herein by reference.

BACKGROUND

1. Technical Field

Aspects of this document relate generally to compositions for synthetic wax ester compositions. More specific implementations involve synthetic compositions to be used in cosmetic products.

2. Background

Conventionally, to obtain jojoba esters with the physical and chemical properties observed, oil must be extracted from the collected seeds of the jojoba plant. The oil is then processed through a transesterification process.

SUMMARY

Implementations of wax ester compositions may include: a product of transesterifying three esters derived from fatty acids and fatty alcohols using one of a chemical catalyst, an enzyme catalyst, a bio-based catalyst or any combination thereof. The ratio of the three esters in the mixture prior to transesterification is one of 65%/23%/12%, 56%/29%/15%, or 36%/34%/30%, of a first ester, a second ester, and a third ester respectively, measured by weight of the mixture. The product may demonstrate a substantially equivalent physical property to a physical property of a transesterified wax ester composition including a jojoba ester.

Implementations of wax ester compositions may include one, all, or any of the following:

The product may demonstrate an equivalent sensory attribute to the transesterified wax ester composition comprising the jojoba ester.

The product may demonstrate an equivalent functional attribute to the transesterified wax ester composition comprising the jojoba ester.

The three esters are derived from fatty acids including oleic acid, stearic acid, and behenic acid, and from fatty alcohols comprising oleyl alcohol, stearyl alcohol, and behenyl alcohol, respectively.

The physical property may be one of iodine value and dropping point.

The average molecular weight of the product may be less than an average molecular weight of the transesterified wax ester composition including the jojoba ester.

The sensory attribute may be one of feel, texture, or playtime.

The functional attribute may be viscosity, color, or stability.

The three esters have carbon chain lengths between 18 to 22 carbons.

The carbon chain length distribution may range between 34 to 44 carbons in length with a peak at 36 carbons.

The transesterified wax ester composition including the jojoba ester may have a carbon chain length distribution range between 36 to 46 carbons with a peak at 42 carbons.

Implementations of wax ester compositions may include: a synthetic product of three or more esters derived from fatty acids and fatty alcohols using one of a chemical catalyst, an enzyme catalyst, a bio-based catalyst, or any combination thereof. The synthetic product may demonstrate a substantially equivalent physical property to a physical property of a transesterified wax ester composition including a botanically derived jojoba ester.

Implementations of wax ester compositions may include one, all, or any of the following:

The synthetic product may comprise a carbon chain length distribution range between 34 to 44 carbons in length with a peak at 36 carbons and the transesterified wax ester composition including the jojoba ester may have a carbon chain length distribution range between 36 to 46 carbons with a peak at 42 carbons.

The synthetic product may demonstrate an equivalent sensory attribute to the transesterified wax ester composition including the jojoba ester.

The synthetic product may demonstrate an equivalent functional attribute to the transesterified wax ester composition including the jojoba ester.

The physical property may be one of iodine value or dropping point.

The average molecular weight of the synthetic product is less than an average molecular weight of the transesterified wax ester composition including the jojoba ester.

The sensory attribute may be one of feel, texture, or playtime.

The functional attribute may be viscosity, color, or stability.

The peak carbon chain length of the synthetic product may be 36 carbons.

Implementations of a wax ester composition may include a product of transesterifying a first ester and a second ester where the first ester and the second ester are each derived from fatty acids and fatty alcohols using a chemical catalyst, an enzyme catalyst, a bio-based catalyst, or any combination thereof. The ratio of the first ester to the second ester in the mixture prior to transesterification may be 33.3% to 66.7% measured by weight of the mixture. The product may demonstrate a substantially equivalent physical property to a physical property of a transesterified wax ester composition comprising a jojoba ester.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

Figure 1:
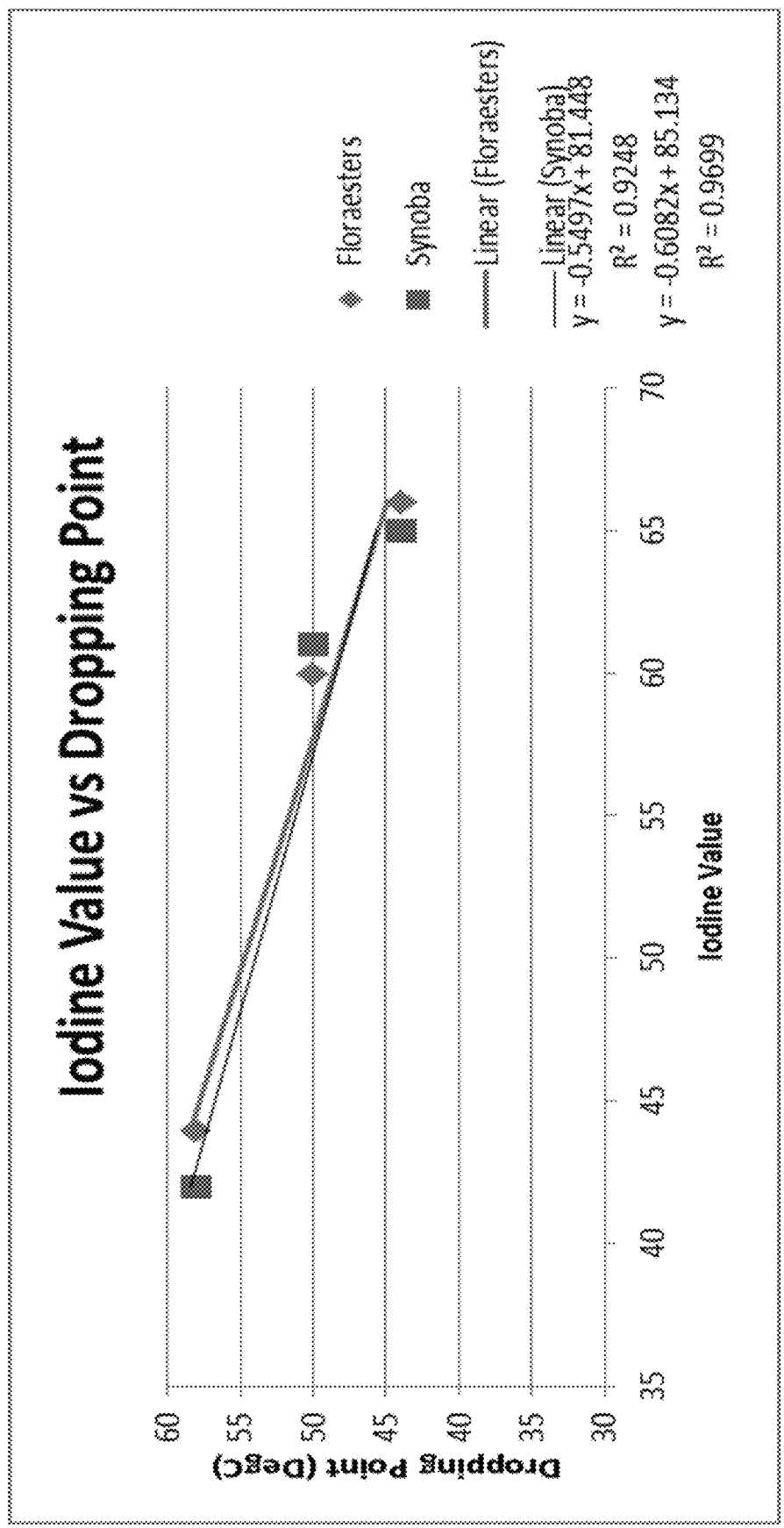
FIG. 1 is a graph comparing the Iodine Value and Dropping Point of implementations of a synthetic wax ester composition and botanically derived jojoba esters.

This disclosure, its aspects and implementations, are not limited to the specific components, assembly procedures or method elements disclosed herein. Many additional components, assembly procedures and/or method elements known in the art consistent with the intended wax ester compositions will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such wax ester compositions and implementing components and methods, consistent with the intended operation and methods.

Implementations of wax ester compositions as described herein replicate the sensory and functional attributes of jojoba based products categorized as jojoba esters by the International Nomenclature of Cosmetics Ingredients (INCI). The implementations of wax esters disclosed herein are synthetic as they are not naturally observed. In various implementations, the attributes of synthetic wax ester compositions may include feel, texture, playtime, dropping point, iodine value, viscosity, color and stability. Implementations of wax ester compositions may replicate the sensory and functional attributes of jojoba ester products marketed under the tradenames of FLORAESTERS 20, FLORAESTERS 30 and FLORAESTERS 60 by International Flora Technologies, Ltd. of Chandler, Ariz.

Implementations of wax ester compositions disclosed herein may be synthesized using a combination of two or more esters in specific ratios that display various attributes originally only seen in jojoba esters which come from the seed of the jojoba plant. The starting materials for implementations of wax ester compositions as described herein include oleyl oleate, stearyl stearate, and behenyl behenate. In other implementations, a wax ester composition may include two or more esters derived from fatty acids and fatty alcohols. In various implementations the fatty acids may include oleic acid, stearic acid, and behenic acid, and the fatty alcohols may include oleyl alcohol, stearyl alcohol, and behenyl alcohol. The two or more esters may include carbon chain lengths between 18 to 22 carbons. In other implementations, the two or more esters may include carbon chain length distribution ranges between 34 to 44 carbons. In some implementations, individual fatty alcohols and fatty acids may be used in lieu of esterified wax ester starting materials. Examples of additional suitable individual fatty alcohols and fatty acids from various sources that may be used in various implementations include, by non-limiting example, triglycerides, caprylic, octyldodecanol, ethylhexyl palmitate, dicaprylyl carbonate, sunflower oil (high oleic acid content), coconut oil, palm kernel oil, cocoa butter, avocado oil, palm oil, olive oil, almond oil, neem oil, canola oil, borage oil, sesame oil, wheat germ, corn oil, soybean oil, sunflower oil (low oleic content), kukui, chia seed oil, grape seed oil, rice bran oil, hemp oil, safflower oil, and other ester-containing oils useful as ingredients for cosmetics.

Oleyl oleate is an ester of oleyl alcohol and oleic acid. Oleyl oleate has a chemical formula of $C_{36}H_{68}O_2$, a molecular weight of 532.94 g/mol, and a melting point of 14-16 degrees Celsius. Oleyl oleate may be derived from, by non-limiting example, various animal fats, vegetable fats, oils including olive oil, wheat germ oil, coconut oil, flaxseed oil, almond oil, safflower oil, and the like or any combination thereof. It may also be obtained commercially from inedible tallow which may be rendered from the fat of beef or mutton. It may also be possible to obtain oleyl oleate from purely synthetic sources through chemical reaction from various precursors. Oleyl oleate is a liquid and may be used in foods, soft soaps, bar soaps, permanent wave hair solutions, creams, nail polish, lipsticks, hair conditioning agents, skins conditions agents and as an emollient. Oleyl oleate may also be listed as (Z)-octadec-9-enyl oleate; 9-octadecenoic acid (9Z); (9Z)-9-octadecenyl ester; 9-octadecenoic acid, 9-octadecenyl ester; 9-octadecenyl ester 9-octadecenoic acid; 9-octadecenoic acid (Z); 9-octadecenyl ester, (Z); oleic acid, oleyl ester; or oleyl ester oleic acid. Derivatives of oleyl oleate may include oleyl stearate and oleyl palmitate.

Stearyl stearate is an ester of stearyl alcohol and stearic acid. Stearyl stearate has a chemical formula of $C_{36}H_{72}O_2$ and a molecular weight of 536.97 g/mol. Stearyl stearate may be prepared from, by non-limiting example, whale oil, animal fats, vegetable oil, plant sources, cocoa butter and shea butter. It may also be possible to obtain stearyl stearate from purely synthetic sources through chemical reaction from various precursors. Stearyl stearate is a mixture of solid alcohols and may be used in medicines, creams, rinses, shampoos, and other similar products. Stearyl stearate may also be listed as, by non-limiting example, octadecanoic acid, octadecyl ester; octadecanoic acid, octadecyl ester, stearic acid, stearyl ester, octadecyl ester octadecanoic acid, and octadecyl stearate. Derivatives of stearyl stearate may include stearamine oxide, stearyl acetate, stearyl caprylate, stearyl citrate, stearyldimethyl amine, stearyl glycyrrhetinate, stearyl heptanoate, stearyl octanoate, and stearyl stearate.

Behenyl behenate is an ester of behenyl alcohol and behenic acid. Behenyl behenate has a chemical formula of $C_{44}H_{88}O_2$ and a molecular weight of 649.19 g/mol. Behenyl behenate may be derived from, by non-limiting example, seeds of the Ben-oil tree (*Moringa oleifera*), oils and oil bearing plants including pracaxi oil, rapeseed oil, canola oil, peanut oils and peanut skins. It may also be possible to obtain behenyl behenate from purely synthetic sources through chemical reaction from various precursors. Behenyl behenate is a dry powder and may be used in hair conditioners, moisturizers, lubricating oils, anti-foaming agents, floor polishes and candles. Behenyl behenate may also be listed as docosyl docosanoate; docosanyl docosanoate; docosanoic acid, docosyl ester, docosyl behenate, Pelemol BB, and Kester Wax BB.

Implementations of wax ester compositions like those disclosed herein are manufactured by combining oleyl oleate, stearyl stearate, and behenyl behenate in specific ratios by measured weight. In a particular implementation, the ratios are 56% oleyl oleate, 23% stearyl stearate, and 12% behenyl behenate. In another implementation, the ratio is 56% oleyl oleate, 29% stearyl stearate, and 15% behenyl behenate. In another implementation, the ratio is 36% oleyl oleate, 34% stearyl stearate, and 30% behenyl behenate. These various implementations are listed in Table 1 below. Once combined in any of the previously mentioned ratios in this document, the composition is then transesterified through a chemical process, bio-based catalyst process, enzyme catalyst process, any combination thereof, or any other known processes in the art. An explanation of transesterifying through the use of a catalytic process may be found in U.S. patent application Ser. No. 14/841,242 by Jeff Addy et al, titled "Processes and Systems for Catalytic Manufacture of Wax Ester Derivatives," filed Aug. 31, 2015, and published as U.S. Patent Publication 20160177350, the disclosure of which is incorporated entirely herein by reference.

Without being bound by any theory, it is believed that the synthesis of wax ester compositions through the transesterification of these materials in appropriate ratios achieves the completely unexpected result of demonstrating a substantially equivalent physical property to a transesterified wax ester composition derived from jojoba esters. For example, the synthesized wax ester compositions disclosed herein demonstrate an equivalent sensory attribute to a transesterified wax ester composition including jojoba ester. The sensory attributes of the product may include a substantially equivalent feel, texture, or playtime to the transesterified wax ester composition including jojoba ester. The synthesized wax ester product demonstrates an equivalent functional attribute to the transesterified wax ester composition including the jojoba ester. By non-limiting example, the functional attributes of the product may include viscosity, color, or stability. Implementations of wax ester compositions as described herein may be utilized as cost effective substitutions having the attributes associated with jojoba ester products including the FLORAESTERS 20, FLORAESTERS 30 and FLORAESTERS 60.

TABLE 1

| Material | Oleyl Oleate C36:2 | Stearyl Stearate C36:0 | Behenyl Behenate C44:0 |
|---|---|---|---|
| SYNOBA20 | 65% | 23% | 12% |
| SYNOBA30 | 56% | 29% | 15% |
| SYNOBA60 | 36% | 34% | 30% |
| SYNOBA70 | 0.0% | 33.3% | 66.7% |

The implementations of wax esters products were surprisingly shown to replicate the physical properties of the jojoba esters as well. In one example, the physical properties included the dropping points of the product. The synthesized wax ester products were shown to replicate the dropping point of the jojoba esters while having similar iodine values and despite having lower molecular weights as illustrated in Table 2. The unsaturation within the molecules would specifically be expected to be in the cis configuration. One skilled in the art would expect a wax ester based lipid with equal degrees of unsaturation and iodine values to have similar dropping points. One skilled in the art would also expect a higher molecular weight species to have a higher dropping point compared to a lower molecular weight compound with a similar iodine value. The implementations of wax ester compositions, labeled SYNOBA in the tables, did not exhibit these expected characteristics instead the SYNOBA compounds have lower average molecular weights than the naturally derived jojoba esters while having the same dropping point. This is a completely unexpected result.

TABLE 2

| Material | Iodine Value | Avg. Molecular Wt. (g/mol) | Dropping Point (° C.) |
|---|---|---|---|
| SYNOBA 20 | 65 | 540.6 | 44 |
| SYNOBA 30 | 61 | 544.1 | 50 |
| SYNOBA 60 | 42 | 552.9 | 58 |
| FLORAESTERS 20 | 66 | 612.2 | 44 |
| FLORAESTERS 30 | 60 | 612.7 | 50 |
| FLORAESTERS 60 | 44 | 613.7 | 58 |

Figure 2:
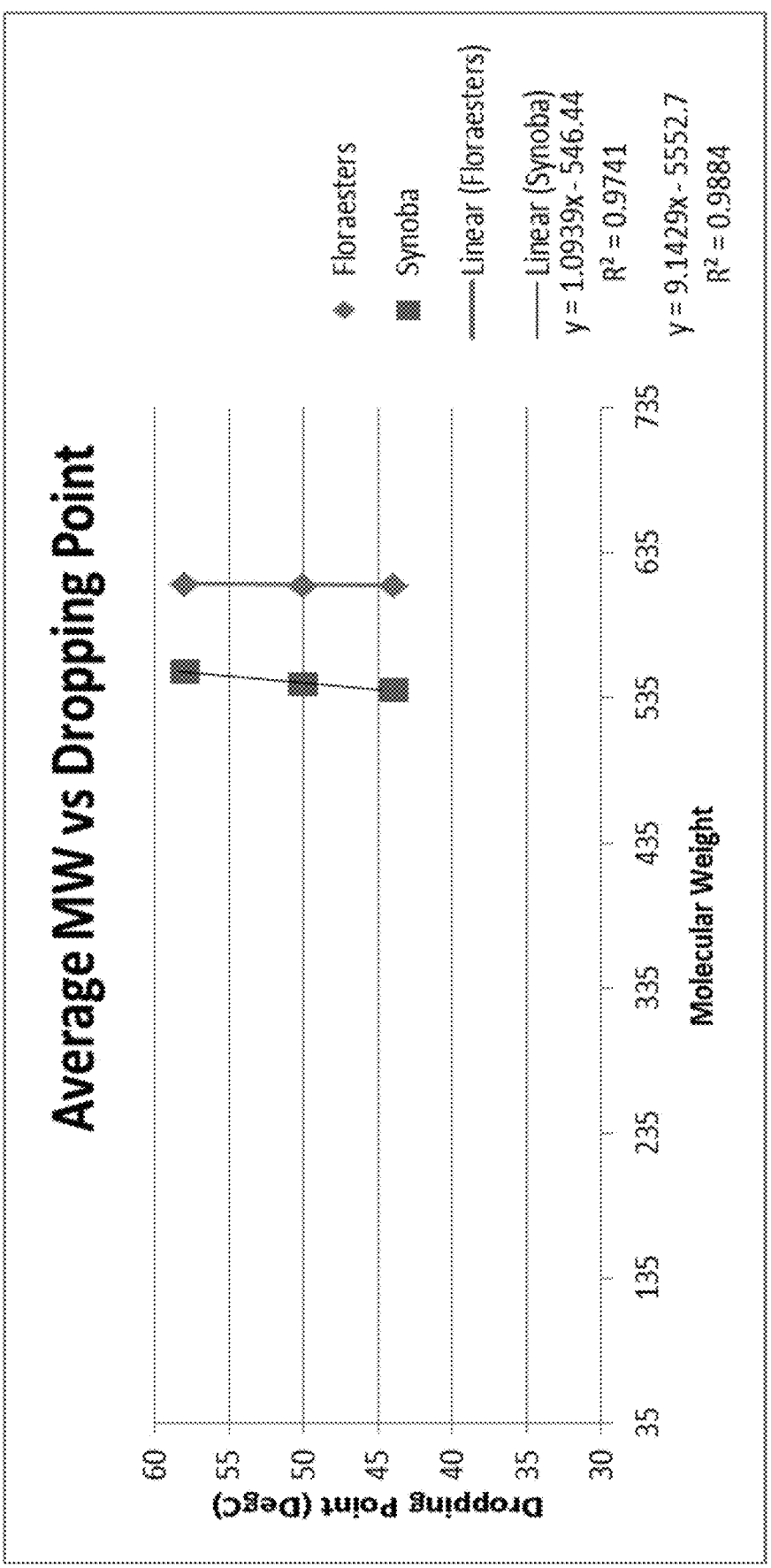
FIG. 2 is a graph comparing the Average Molecular Weight and Dropping point of implementations of a synthetic wax ester composition and botanically derived jojoba esters.

Referring now to FIG. 1, the graph illustrates that the SYNOBA compositions have similar iodine values and dropping points when compared to the FLORAESTERS compounds. Referring to FIG. 2, the graph illustrates that the SYNOBA compounds have the same dropping point as the FLORAESTERS compounds while having substantially lower molecular weights. The figures indicate that the dropping point has a higher dependency on the iodine value when compared to the average molecular weight of the compositions. Without being bound by any theory, it is believed that the slopes generated in FIG. 1 and FIG. 2 are nearly the same due to the polymorphism characteristics of partially saturated wax ester compositions. Polymorphism is the ability of solid materials including crystals to exist in more than one form or crystal structure. Double bonds in the cis configuration inhibit crystallization by interrupting the stacking mechanism of crystal formation due to the larger intermolecular forces and bulkier molecular structure typically present in cis configurations. The only source of unsaturation in the compositions disclosed in this document is from the oleyl alcohol and oleic acid. Those skilled in the art would understand that jojoba oil has much more variation in unsaturated fatty alcohols and fatty acids. Both unsaturated fatty alcohols and fatty acids are evenly distributed among all the present wax esters during the transesterification reaction for both products. The more consistent unsaturated wax esters of the compositions disclosed in this document are believed to lead to more efficient packing of the molecules and therefore a more stable polymorph when compared to jojoba-derived equivalents. The tightly packed wax ester polymorphs of the compositions disclosed in this document have a higher heat of crystallization leading to the unexpected observation of a higher dropping point despite having a lower average molecular weight but equal degree of unsaturation.

Figure 3:
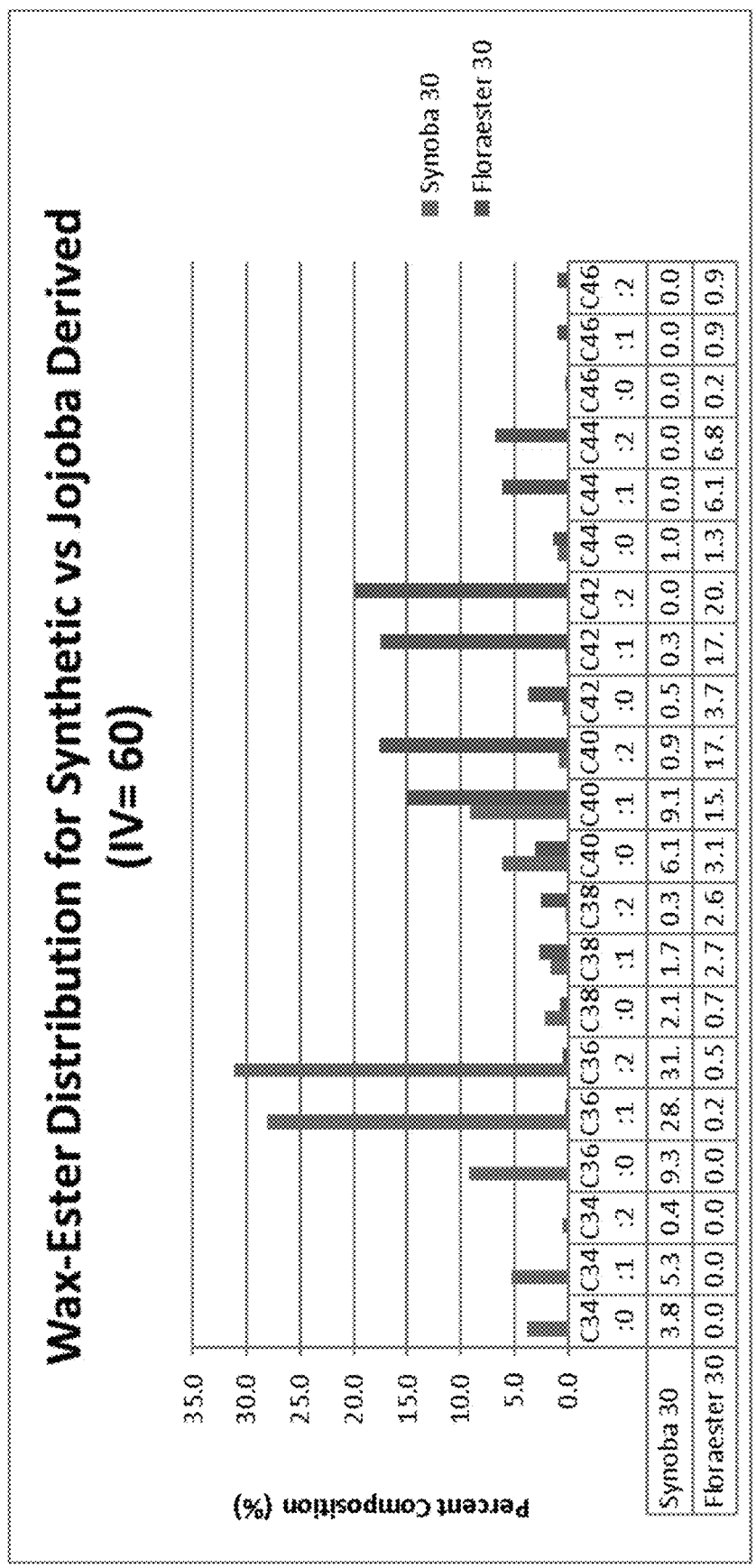
FIG. 3 is a graph comparing the Wax Ester Distribution of implementations of synthetic wax ester compositions and botanically derived jojoba esters each having an iodine value of 66.
Figure 4:
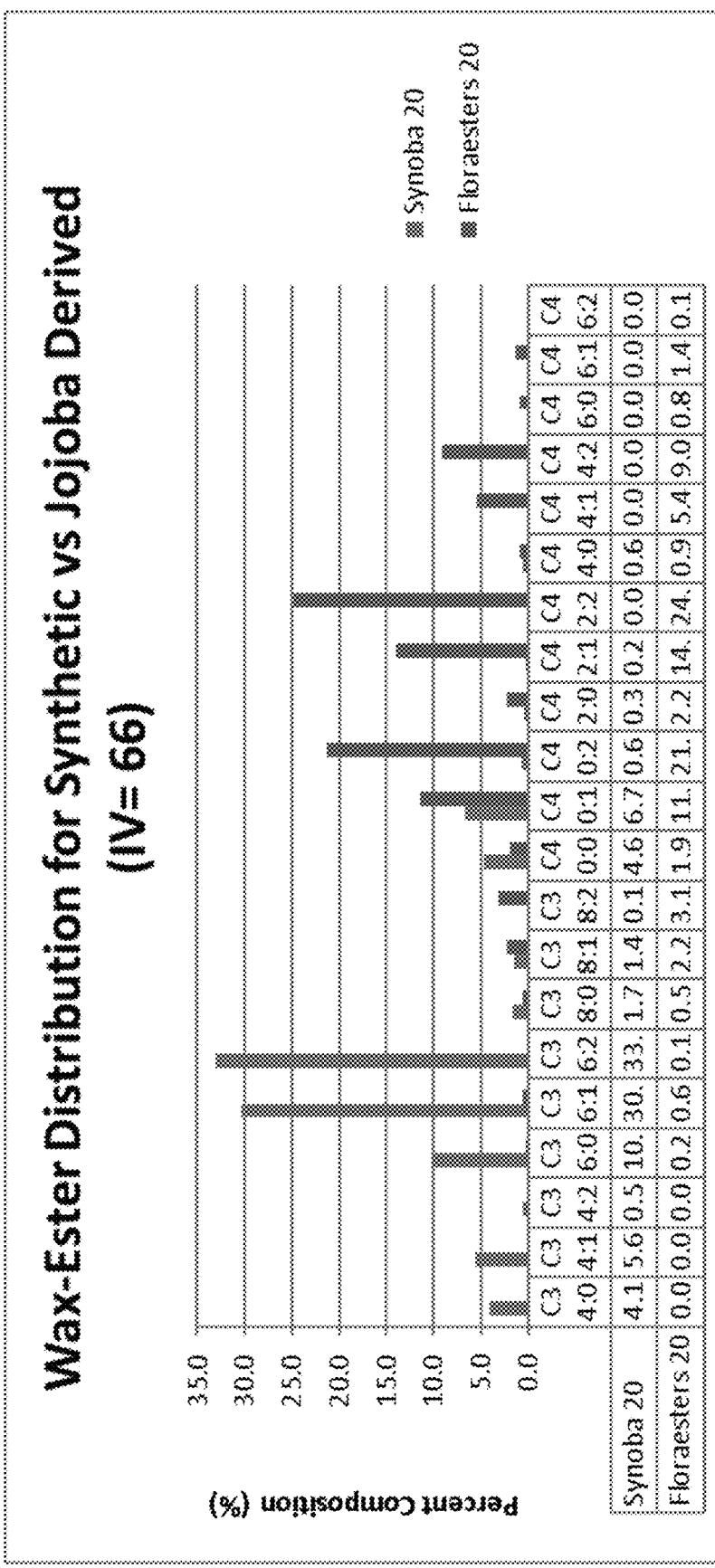
FIG. 4 is a graph comparing the Wax Ester Distribution of implementations of synthetic wax ester compositions and botanically derived jojoba esters each having an iodine value of 60.
Figure 5:
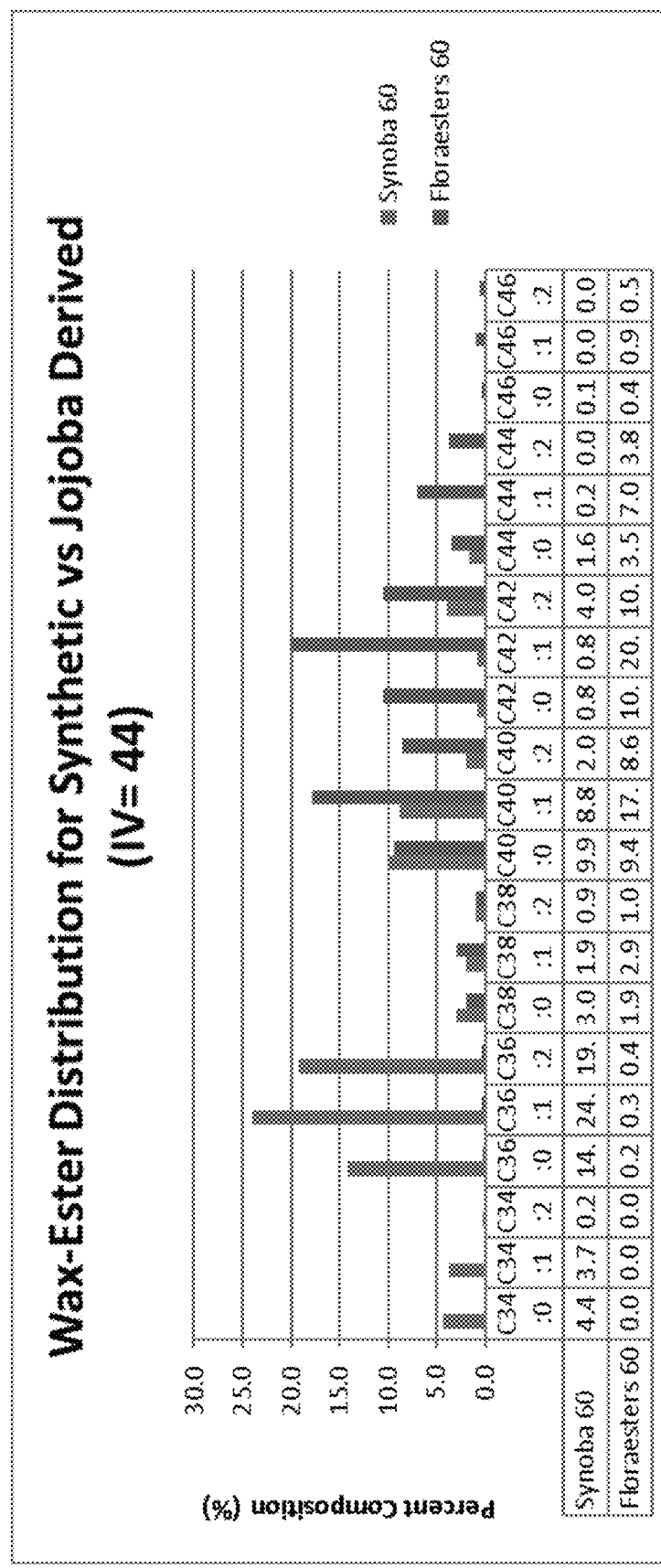
FIG. 5 is a graph comparing the Wax Ester Distribution of implementations of synthetic wax ester compositions and botanically derived jojoba esters each having an iodine value of 44.

Referring to FIGS. 3, 4 and 5, the distribution of the individual wax ester species of compositions disclosed in this document and the FLORAESTERS compositions referred to previously is illustrated. Referring to FIG. 3, the composition illustrated (SYNOBA 20) has an iodine value of 66. Referring to FIG. 4, the composition illustrated (SYNOBA 30) has an iodine value of 60. Referring to FIG. 5, the composition (SYNOBA 60) illustrated has an iodine value of 44. These charts illustrate that the synthesized wax ester products disclosed herein have a smaller carbon chain length distribution compared to the jojoba esters. The wax ester products are shown to have a peak carbon chain length of 36 carbons while the carbon chain length distribution ranges between 34 to 44 carbons in length. The carbon chain lengths of the wax ester products are smaller on average than the jojoba ester compounds which have a carbon chain length distribution range between 36 to 46 carbons with a peak at 42 carbons.

Additionally, the implementations of wax esters had similar functionality when used in a cosmetics formulation. Referring to Table 3, a composition like that disclosed herein (SYNOBA 20) and that marketed as FLORAESTERS 20 were put into the formulations shown. The formulated SYNOBA 20 and FLORAESTERS 20 lotions had a similar feel, viscosity, texture, color and stability. An additional formulation test was conducted with the same formula to compare SYNOBA 30 and FLORAESTERS 30. Again, the aesthetics and stability were similar, further showing that the compositions disclosed herein are suitable substitutes for those marketed under the FLORAESTERS tradename and other jojoba ester products and compositions despite having a different wax ester profile and average molecular weight. Therefore, the compositions like those disclosed herein may be suitable for use in cosmetics such as lotions, facial cleansers, moisturizers, makeup removers, lip conditions, shaving gels, or similar applications as a substitute for jojoba oil and jojoba ester containing compositions.

TABLE 3

| Phase | Trade Name | INCI | Supplier | SYNOBA 20 % wt./wt. | FLORAESTERS 20 % wt./wt. |
|---|---|---|---|---|---|
| A | Deionized Water | Water | — | 66.27 | 66.27 |
|   | Versene ® Na2 Crystals | Disodium EDTA | The Dow Chemical Co. | 0.03 | 0.03 |
| B | Glycerin, USP | Glycerin | The Dow Chemical Co. | 5.00 | 5.00 |
|   | Keltrol ® CG-T | Xantham Gum | CP Kelco | 0.30 | 0.30 |
| C | Floramac *Macadamia* Oil | *Macadamia Intefrifolia* Seed Oil | Floratech | 3.00 | 3.00 |
|   | FLORAESTERS 20 or SYNOBA 20 |  | Floratech |  | 3.00 |
|   | Radia 7779 | Ethyhexyl Palmitate | Oleon | 3.00 | 3.00 |
|   | Biochemica Cocoa Butter White | *Theobroma Cacao* (Cocoa) Seed Butter | Hallstar | 5.00 | 5.00 |
|   | Florasun 90 | *Helianthus Annuus* (Sunflower) Seed Oil | Floratech | 2.00 | 2.00 |
|   | Botanisil ® CP-33 | Cyclopentasiloxane | Botanigenics, Inc. | 4.00 | 4.00 |
|   | Dow Corning ® 200 Fluid | Dimethicone | Dow Corning Corporation | 0.50 | 0.50 |
|   | Lexemul ® 561 | Glyceryl Stearate (and) PEG-100 Stearate | Inolex Chemicals | 4.00 | 4.00 |
|   | Emulgade PL ® 68/50 | Cetearyl Glucoside (and) Cetearyl Alcohol | Cognis Corporation | 3.00 | 3.00 |
| D | Phenonip ® | Phenoxyethanol (and) Methylparaben (and) Ethylparaben (and) Butylparaben (and) Propylparaben (and) Isobutylparaben | Clariant Corporation | 0.90 | 0.90 |
|   |  |  | Total | 100 | 100 |

TABLE 4

|  | Oleyl Oleate | | Stearyl Stearate | | Behenyl Behenate | |
|---|---|---|---|---|---|---|
|  | min | max | min | max | min | max |
| SYN20 | 64 | 70 | 19 | 24 | 10 | 14 |
| SYN30 | 55 | 61 | 20 | 25 | 13 | 16 |
| SYN60 | 35 | 40 | 31 | 33 | 28 | 32 |
| SYN70 | 0 | 0 | 30 | 35 | 65 | 70 |

Table 4 lists the ranges of weight percentages for each component of the total mixture pre-transesterification in which the results observed in this document regarding the similar properties document in this document have been observed.

In places where the description above refers to particular implementations of wax ester compositions and implementing components, sub-components, methods and sub-methods, it should be readily apparent that a number of modifications may be made without departing from the spirit thereof and that these implementations, implementing components, sub-components, methods and sub-methods may be applied to other wax ester compositions.

What is claimed is:

1. A wax ester composition comprising:
    a synthetic product of transesterifying three or more esters derived from fatty acids and fatty alcohols using one of a chemical enzyme, an enzyme catalyst, a bio-based catalyst, or any combination thereof;
    wherein the synthetic product demonstrates an iodine value in a range between 42 and 65 and a dropping point substantially equivalent to that of a transesterified wax ester composition comprising a botanically derived jojoba ester.

2. The composition of claim 1, wherein the synthetic product comprises esters with a carbon chain length distribution range between 34 to 44 carbons in length with a peak at 36 carbons and the transesterified wax ester composition comprising the jojoba ester comprises esters with a carbon chain length distribution range between 36 to 46 carbons with a peak at 42 carbons.

3. The composition of claim 1, wherein the synthetic product comprises a sensory attribute equivalent to the transesterified wax ester composition comprising the jojoba ester, the sensory attribute comprising one of feel, texture, or playtime.

4. The composition of claim 1, wherein the synthetic product demonstrates a functional attribute equivalent to the transesterified wax ester composition comprising the jojoba ester, the functional attribute comprising one of viscosity, color, or stability.

5. The composition of claim 1, wherein an average molecular weight of esters of the synthetic product is less than an average molecular weight of esters of the transesterified wax ester composition comprising the jojoba ester and the peak carbon chain length of esters of the synthetic product is 36 carbons.

6. A wax ester composition comprising:

a synthetic product of transesterifying three or more esters derived from fatty acids and fatty alcohols using one of a chemical enzyme, an enzyme catalyst, a bio-based catalyst, or any combination thereof;

wherein the synthetic product demonstrates a dropping point between 44 C and 58 C and an iodine value substantially equivalent to that of a transesterified wax ester composition comprising a botanically derived jojoba ester.

7. The composition of claim 6, wherein the synthetic product comprises esters with a carbon chain length distribution range between 34 to 44 carbons in length with a peak at 36 carbons and the transesterified wax ester composition comprising the jojoba ester comprises esters with a carbon chain length distribution range between 36 to 46 carbons with a peak at 42 carbons.

8. The composition of claim 6, wherein the synthetic product comprises a sensory attribute equivalent to the transesterified wax ester composition comprising the jojoba ester, the sensory attribute comprising one of feel, texture, or playtime.

9. The composition of claim 6, wherein the synthetic product demonstrates a functional attribute equivalent to the transesterified wax ester composition comprising the jojoba ester, the functional attribute comprising one of viscosity, color, or stability.

10. The composition of claim 6, wherein an average molecular weight of esters of the synthetic product is less than an average molecular weight of esters of the transesterified wax ester composition comprising the jojoba ester and the peak carbon chain length of esters of the synthetic product is 36 carbons.

* * * * *